United States Patent [19]

O'Brien et al.

[11] 4,036,840

[45] July 19, 1977

[54] 2-SUBSTITUTED-S-TRIAZOLO[1,5A]-PYRIMIDINES

[75] Inventors: Darrell E. O'Brien, Mission Viejo; Thomas Novinson, Costa Mesa; Robert H. Springer, Santa Ana, all of Calif.

[73] Assignee: ICN Pharmaceuticals, Irvine, Calif.

[21] Appl. No.: 579,832

[22] Filed: May 22, 1975

Related U.S. Application Data

[63] Continuation-in-part of Ser. No. 260,517, June 7, 1972, abandoned.

[51] Int. Cl.² .......................................... C07D 239/00
[52] U.S. Cl. .................... 260/256.5 R; 260/247.1 L; 424/248.52; 424/251
[58] Field of Search .................. 260/256.5 R

[56] References Cited

U.S. PATENT DOCUMENTS 2,449,225  9/1948  Heimbach et al. .................. 95/7
2,566,659  9/1951  Fry .................................... 95/7
2,933,388  4/1960  Knott ................................ 96/61

Primary Examiner—Leonard Schenkman
Attorney, Agent, or Firm—Kay H. Boswell

[57] ABSTRACT

2-Substituted-s-triazolo[1,5a]pyrimidines are disclosed which are useful as inhibitors of phosphodiesterase enzymes or intermediates in the production process. Such compounds are of the following structure:

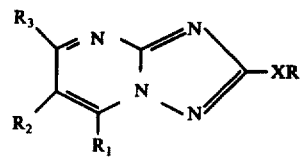

wherein X, R, $R_1$, $R_2$ and $R_3$ are as defined hereinafter.

12 Claims, No Drawings

2-SUBSTITUTED-S-TRIAZOLO[1,5a]PYRIMIDINES

CROSS REFERENCE TO RELATED APPLICATIONS

This is a continuation-in-part of our application Ser. No. 260,517, filed June 7, 1972, and now abandoned.

BACKGROUND OF THE INVENTION

As reported by Sutherland et al., in "Cyclic AMP," Am. Rev. Biochem. 37, 149 (1968), cyclic adenosine monophosphate (C-AMP) has been established as an intracellular "second messenger," mediating many of the actions of a variety of different hormones. According to this theory, first messenger hormones, epinephrine and norepinephrine, influence adenyl cyclase contained at or within cell walls to form intracellulary, cyclic AMP from adenosine triphosphate upon receipt of the extra-cellular hormone signal. The formed cyclic AMP in turn functions as a second messenger and stimulates intracellular functions particularly to the target cells of the hormone. Cyclic AMP has thus been shown to "activate" protein kinases, which in turn produce physiological effects such as muscle contraction, glycogenolysis, steroidogenesis and lipolysis.

Cyclic AMP is degraded, however, in vivo by phosphodiesterase enzymes, which catalyze hydrolysis of the cyclic purine nucleotide to 5'-adenosine monophosphate with a consequent loss of function. It has accordingly be suggested that substituted cyclic AMP analogs which are more resistant to phosphodiesterase degradation than the naturally occurring cyclic nucleotide might be administered in aid of lagging cellular processes. Synthetic production of such compounds, however, is quite costly. It would be advantageous, therefore, to enhance the beneficial effects of naturally produced cyclic AMP by administering compounds which are capable of inhibiting the undesirable effects of phosphodiesterase enzymes.

Sutherland et al., in Circulation 37, 279 (1968), suggest that the pharmacological effects of theophylline, which has the structure

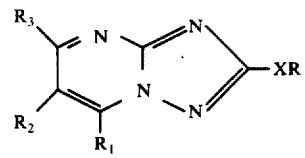

are the result of its ability to inhibit the action of phosphodiesterase enzymes. Theophylline has thus been employed in lieu of the adenyl cyclase-stimulating hormones, epinephrine and norepinephrine, as a heart stimulant following cardiac arrest and in refractory asthma cases as a bronchial dilator. Theophylline, however, does not selectively inhibit phosphodiesterase, but rather gives general stimulation to the central nervous system. Accordingly, the use of theophylline can make the recipient nervous and irritable and can also create cardiovasular effects, i.e., rapid beating. By the same token, theophylline is not as potent as a phosphodiesterase inhibitor as is desired and consequently has to be used in larger quantities, which, of course, can further the undesirable effects enumerated above.

As indicated in the application of Darrell E. O'Brien et al., Ser. No. 206,538, entitled "3,5,7-trisubstituted pyrazolo[1,5a]pyrimidines," assigned to the same assignee as this application, various 5,7 -dialkyl- and 5-alkyl-3,7-disubstitutedpyrazolo[1,5a]pyrimidines have been found to possess phosphodiesterase inhibition properties. Further evaluation of such compounds has shown that 3-bromo-5,7-dimethylpyrazolo[1,5a]pyrimidine not only is significantly more active than theophylline against various phosphodiesterase enzymes, but also has the ability to produce a positive inotropic effect in an anesthetized dog, which has accordingly led to the investigation of additional derivatives of such pyrazolo[1,5a] pyrimidine ring system, including 6-carbethoxy-pyrazolo[1,5a]pyrimidines set forth in the application of Darrell E. O'Brien et al., entitled "6-carbethoxy-3,7-disubstitutedpyrazolo[1,5a]pyrimidines" and assigned to the same assignee as this application, and the triazolo[1,5a]pyrimidine ring system of this invention.

SUMMARY OF THE INVENTION

Compounds of the following structure are provided which are capable of inhibiting the enzyme phosphodiesterase, bringing about coronary dilation, producing positive cardiac inotropic response and have smooth muscle relaxant, anti-inflammatory and hypotensive properties:

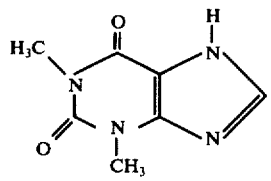

wherein X is sulfur, oxygen, nitrogen or carbon atom or sulfonyl; R is an alkyl, aralkyl, aryl, heteroaromatic or polynuclear aromatic or X and R are joined together to form a heterocyclic ring; $R_1$ is alkyl, OH, halogen, an amine, amine salt or mercapto; $R_2$ is H or carbethoxy; and $R_3$ is alkyl or H. When $R_2$ is carbethoxy, $R_3$ is H and when $R_1$ is OH, halogen or mercapto, $R_2$ is carbethoxy and when R is methyl, $R_3$ is H.

In a more preferred group of compounds X is thio or sulfonyl; R is alkyl or an aromatic or substituted aromatic nucleus, as for example, benzyl, substituted benzyl, heteroaromatic, or polynuclear aromatic; $R_1$ is $C_2$–$C_6$ alkyl, an amine, amine salt; $R_2$ is H or carbethoxy; and $R_3$ is $C_1$–$C_6$ alkyl or H. When $R_2$ is carbethoxy, $R_3$ is H.

As will be seen from the following description and examples, R may be an alkyl, including branched or substituted alkyls such as Compounds 8, 10, 21 and 22. Preferably, the alkyl group will contain from two to six carbon atoms. R may also be an aromatic substituent or a substituted aromatic nucleus such as benzyl, substituted benzyl (Compounds 4, 12–15, 42, 44, 45), heteroaromatic (Compound 20, 46, 47, 51), polynuclear aromatic (Compounds 17 and 20) and aralkyl (Compound 23). $R_1$ may be an NHR', $N(R')_2$ or N-N(R')$_2$ amine such as Compounds 26, 33, and 37–39 where R' is preferably a $C_1$ to $C_6$ alkyl or substituted alkyl, or piperidino (Compound 30) and morpholine (Compounds 31 and 36) or amine salt (Compound 32, the dihydrochloride salt of hydrazine).

DETAILED DESCRIPTION OF THE INVENTION

The general procedure utilized to produce the compounds of this invention is described in connection with the schematic drawing which follows, the various compounds being indicated by the numbers 1–52 inclusive. Condensation of 3-amino-5-benzylthio-s-trizaole (Compound 1) or 3-amino-5-(p-chlorobenzylthio)-s-triazole (Compound 2) with acetylacetone in ethanol containing piperidine or nonane-4,6-dione in acetic acid yields 2-benzylthio-5,7-dimethyl-s-triazolo[1,5a]pyrimidine (Compound 3), 2-(p-chlorobenzylthio)-5,7-dimethyl-s-triazole[1,5a]pyrimidine (Compound 4) and 2-benzylthio-5,7-di-n-propyl-1,2,4-triazole[1,5a]pyrimidine (Compound 42) respectively. Following the procedure of L. A. Williams, J. Chem. Soc., 1829 (1960), 3-amino-5-mercapto-s-triazole (Compound 5) was condensed with acetylacetone or nonane-4,6-dione in acetic acid to obtain 5,7-dimethyl-2-mercapto-s-triazolo[1,5a]pyrimidine (Compound 6) and 5,7-di-n-propyl-2-mercapto-s-triazolo[1,5a] (Compound 43).

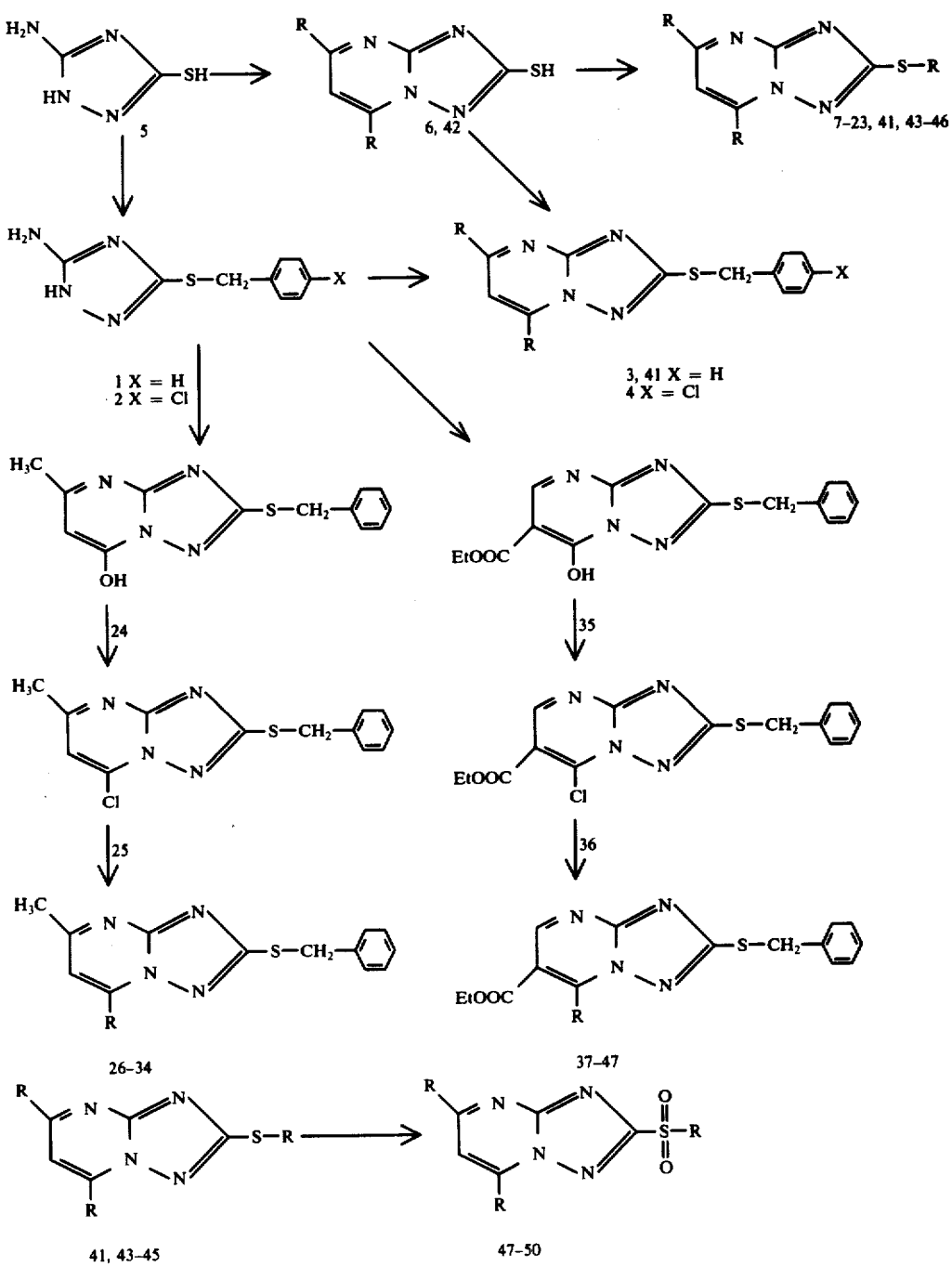

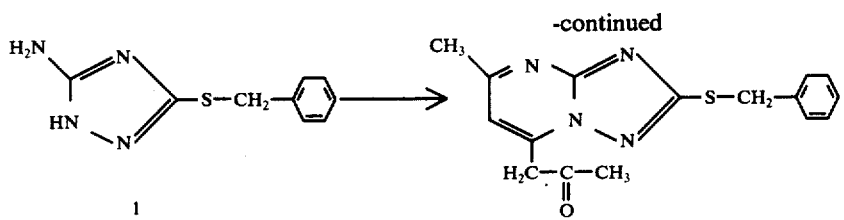

When Compound 6 is treated with benzyl chloride in alkaline solution, Compound 3 is also obtained, which is identical in all respects to the product obtained by direct condensation. Alkylation of Compounds 6 and 43 with alkyl and aralkylhalides yields the alkylthio and aralkylthio derivatives, Compounds 7 through 23 and 44 through 47 inclusive.

Condensation of compound 1 with acetoacetic ester in acetic acid affords 2-benzylthio-7-hydroxy-5-methyl-s-triazolo [1,5a]pyrimidine (Compound 24). Treatment of this compound with refluxing phosphorus oxychloride yields 2-benzylthio-7-chloro-5-methyl-s-triazolo[1,-5a]pyrimidine (Compound 25). Nucleophilic displacement of the chloro moiety of Compound 25 with primary and secondary amines in warm ethanol yields Compounds 26 through 31. Reaction of Compound 25 with hydrazine or unsymmetrical dimethylhydrazine yields 2-benzylthio-6-hydrazino-5-methyl-s-triazolo[1,-5a] pyrimidine (Compound 32) and the corresponding 7-dimethylhydrazino analog (Compound 33) respectively.

Condensation of 3-amino-5-benzylthio-s-triazole (Compound 1) with diethyl ethoxymethylenemalonate yields 2-benzylthio-6-carbethoxy-7-hydroxy-s-triazolo[1,5a]pyrimidine (Compound 36). Treatment of this compound with refluxing phosphorus oxychloride affords a good yield of 2-benzylthio-6-carbethoxy-7-chloro-s-triazolo[1,5a]pyrimidine (Compound 37). The chloro moiety of this compound undergoes nucleophilic displacement with various amines to yield the corresponding amino substituted Compounds 38 through 40. Treatment of Compound 36 with sodium hydrosulfide affords 2-benzylthio-6-carbethoxy-7-mercapto-s-triazolo[1,5a]pyrimidine (Compound 42).

Oxidation of Compounds 42, 44 through 46 with m-chloroperbenzoic acid yields the respective sulfonyl derivatives Compounds 48, 49 through 51.

Condensation of 3-amino-5-benzylthio-s-triazole (Compound 1) with heptane-2,4,6-trione yields 2-benzylthio-5-methyl-7-(acetonyl)-1,2,4-triazole[1,5a]-pyrimidine.

The invention will further be understood by reference to the specific but illustrative examples which follow. In all such examples, parts and percentages are by weight and temperatures are in degrees Centigrade unless otherwise indicated. Melting points were taken on a Thomas-Hoover melting point apparatus and are uncorrected. All samples displayed a single spot on thin layer chromatography and were analyzed by the Heterocyclic Chemical Corporation of Harrisonville, Missouri. Where analyses are indicated only by symbols of the elements or functions, analytical results obtained for those elements or functions were within ±0.4% of the theoretical values.

EXAMPLE I

PREPARATION OF 3-AMINO-5-(p-CHLOROBENZYLTHIO)-s-TRIAZOLE (Compound 2)

A mixture of 3-amino-5-mercapto-s-triazole (Compound 5) [4.64g; 40 mmoles] in 40 ml. of 1N sodium hydroxide was stirred at room temperature while solution of p-chlorobenzylchloride [7.55g; 48 mmoles] in 80 ml of absolute ethanol was added. The mixture was then warmed to 70°-75° and stirred for 30 minutes. The amber colored solution was then evaporated to 40 ml at reduced pressure, diluted with 50 ml of water and chilled overnight. The crude product was separated by filtration, air dried, and recrystallized two times from chloroform to afford 4.3g (45%) of analytically pure product that had a melting point of 107°-8°.

Anal. Calcd. for $C_9H_9N_4SCl$: (C,H,N).

EXAMPLE II

PREPARATION OF 2-ARALKYLTHIO-5,7-DIMETHYL-s-TRIAZOLO[1,5a]PYRIMIDINES (Compounds 3 and 4)

A solution of 3-amino-5-aralkylthio-s-triazole (Compound 1 or 2) (10 mmoles) and acetylacetone [1.0g; 10 mmoles] in 50 ml of glacial acetic acid was stirred and heated at 90° for 3 hours. At the end of this time, the mixture was evaporated to dryness at reduced pressure. The residue was washed with water and recrystallized from aqueous ethanol to afford the analytically pure products that the listed in Table I.

EXAMPLE III

PREPARATION OF 2-ALKYLTHIO AND 2-ARALKYLTHIO-5,7-DIMETHYL-s-TRIAZOLO [1,5a]PYRIMIDINES (Compounds 3,7-23)

A solution of 5,7-dimethyl-2-mercapto-s-triazole[1,-5a] pyrimidine (Compound 6) [1.80g; 10 mmoles] in 25 ml of 0.4N sodium hydroxide solution was stirred at room temperature while a solution of alkyl halide or aralkylhalide (10 mmoles) in 10 ml of methanol was added dropwise. After the addition was complete, the mixture was stirred at room temperature for 3 hours, and the precipitated products separated by filtration. These products were recrystallized from methanol or aqueous methanol to afford the analytically pure samples that are listed in Table I.

EXAMPLE IV

PREPARATION OF 2-BENZYLTHIO-7-HYDROXY-5-METHYL-s-TRIAZOLO[1,5a] PYRIMIDINE (Compound 24)

A mixture of 3-amino-5-benzylthio-s-triazole (Compound 1) [10.3g; 0.05 mole] and ethyl acetoacetate [7.91g; 0.05 mole] in glacial acetic acid was refluxed for 12 hours. At the end of this time, the solution was allowed to cool and the crystalline product was separated by filtration. This product was washed with cold ethanol and dried at 100° to afford the analytically pure product that is listed in Table II.

EXAMPLE V

PREPARATION OF 2-BENZYLTHIO-7-CHLORO-5-METHYL-s-TRIAZOLO[1,5a] PYRIMIDINE (Compound 25)

A mixture of 2-benzylthio-7-hydroxy-5-methyl-s-triazolo [1,5a]pyrimidine [5.4g; 20 mmoles] in 100 ml of phosphorus oxychloride was heated at reflux with gentle stirring. At the end of 1 hour the excess phosphorus oxychloride was removed at reduced pressure and the syrup residue was added slowly to crushed ice (250g) with good stirring. The resulting mixture was extracted with methylene chloride 5(50 ml) and the combined methylene chloride extracts were washed with saturated sodium carbonate solution 2(50 ml) and water 2(50 ml). The methylene chloride extract was dried over sodium sulfate and then quickly filtered through 50 g of basic alumina. The alumina was washed with additional methylene chloride (50 ml). The combined methylene chloride solutions were then evaporated to afford 4.1g of light yellow crystalline product. Recrystallization from chloroform-pentane afforded the analytically pure product that is listed in Table II.

EXAMPLE VI

PREPARATION OF 2-BENZYLTHIO-5-METHYL-7-SUBSTITUTEDAMINO-s-TRIAZOLO[1,5a] PYRIMIDINES (Compounds 26–33)

A solution of 2-benzylthio-7-chloro-5-methyl-s-triazolo[1,5a] pyrimidine (Compound 25) [2.88g; 10 mmoles] and substituted amine [12.5 mmoles] in 30 ml of absolute ethanol was heated at reflux for 3 hours, and then evaporated to dryness. The residue was washed with water and then recrystallized from aqueous ethanol to afford the analytically pure products that are listed in Table II.

A solution of 2-benzylthio-7-hydrazino-5-methyl-s-triazolo [1,5a]pyrimidine (Compound 32) in warm dilute hydrochloric acid was allowed to cool, which affords the dihydrochloride salt of the product that is listed in Table II.

EXAMPLE VII

PREPARATION OF 2-BENZYLTHIO-6-CARBETHOXY-7-HYDROXY-s-TRIAZOLO[1,5a] PYRIMIDINE (Compound 34)

A solution of sodium ethoxide in ethanol (prepared by dissolving sodium [3.0g; 0.13 formula weights] in 250 ml of absolute ethanol) was stirred at room temperature while 3-amino-5-benzylthio-s-triazole (Compound 1) [25.0g; 0.121 mole] and diethyl ethoxymethylenemalonate [28.1g; 0.130 mole] was added. The resulting solution was heated at reflux for 12 hours and then evaporated to dryness. The residue was dissolved in 200 ml of cold water and the pH adjusted to 1 by the addition of dilute hydrochloric acid. The precipitate was separated by filtration, washed with water, and recrystallized from aqueous ethanol to afford the analytically pure product that is listed in Table III.

EXAMPLE VIII

PREPARATION OF 2-BENZYLTHIO-6-CARBETHOXY-7-CHLORO-s-TRIAZOLO[1,5a] PYRIMIDINE (Compound 35)

A solution of 2-benzylthio-6-carbethoxy-7-hydroxy-s-triazolo [1,5a]pyrimidine (Compound 34) [20.1g; 0.06 mole] in 250 ml of phosphorus oxychloride was refluxed for 2 hours. At the end of this time, the excess phosphorus oxychloride was removed at reduced pressure and the residual syrup was added to 250g of crushed ice. The resulting solution was extracted with ether 3(200 ml) and the combined etheral extracts washed with saturated sodium bicarbonate solution (100 ml) and dried over anhydrous sodium sulfate. Evaporation of the ether extract afforded the crude chloro derivative which was purified by recrystallization from n-heptane to afford the analytically pure product that is listed in Table III.

EXAMPLE IX

PREPARATION OF 2-BENZYLTHIO-6-CARBETHOXY-7-SUBSTITUTEDAMINO-s-TRIAZOLO[1,5a]PYRIMIDINES (Compounds 6–39)

A solution of 2-benzylthio-6-carbethoxy-7-chloro-s-triazolo[1,5a]pyrimidine (Compound 35) [1.0g; 2.88 mmole] and substituted amine [5.76 mmole] in 30 ml of ethanol was warmed at 55° for 10 minutes and then stirred at room temperature for 1 hour. This solution was then diluted with 70 ml of water and chilled. The precipitated product was separated by filtration and then recrystallized from aqueous ethanol to afford the analytically pure products listed in Table III.

EXAMPLE X

PREPARATION OF 2-BENZYLTHIO-6-CARBETHOXY-7-MERCAPTO-s-TRIAZOLO[1,5a] PYRIMIDINE (Compound 40)

A suspension of 2-benzylthio-6-carbethoxy-7-chloro-s-triazolo[1,5a]pyrimidine (Compound 35) [1.0g; 2.88 mmole] and sodium hydrosulfide trihydrate [1.10g; 0.01 formula weights] in 20 ml of ethanol was stirred and heated to 55° for 10 minutes. At the end of this time the solution was stirred at room temperature for 2 hours and then diluted with 70 ml of water. The pH of the resulting solution was adjusted to 5 by the addition of glacial acetic acid. The precipitated product was separated by filtration, washed with water, and then recrystallized from aqueous ethanol to afford the analytically pure product listed in Table III.

EXAMPLE XI

PREPARATION OF 2-BENZYLTHIO-5,7-DI-n-PROPYL-1,2,4-TRIAZOLO[1,5a] PYRIMIDINE (Compound 41)

A mixture of 8.24g (0.04 mole) of 3-amino-5-benzylthio-1,2,4-triazole, 6.24g (0.04 mole) of nonane-4,6-dione, and 50 ml acetic acid was refluxed for 4 hours. The solvent was distilled in vacuo and the residue was then distilled to afford 10.5g (77%) of the product, b.p. 295°-297° /5mm, recrystallized from heptane-acetone to afford the analytically pure product listed in Table IV.

EXAMPLE XII

PREPARATION OF 5,7-DI-n-PROPYL-2-MERCAPTO-1,2,4-TRIAZOLO[1,5a] PYRIMIDINE (Compound 42)

A mixture of 4.68g (0.03 mole) of nonane-4,6-dione, 3.48g (0.03 mole) of 3-amino-5-mercapto-1,2,4-triazole, and 50 ml glacial acetic acid was refluxed for 20 hours. The reaction mixture was evaporated in vacuo and the residue was partly dissolved in EtOH and a residue was filtered off. The filtrate was evaporated in vacuo and the residue was recrystallized from EtOAc-heptane to afford the analytically pure product listed in Table IV.

EXAMPLE XIII

PREPARATION OF 2-ARALKYLTHIO-5,7-DI-n-PROPYL-s-TRIAZOLO[1,5a] PYRIMIDINE (Compounds 43–46)

A mixture of 2.36g (0.01 mole) of 5,7-di-n-propyl-2-mercapto-1,2,4-triazolo[1,5a]pyrimidine, (0.01 mole) of an aralkyl halide and a solution of 1 g of sodium hydroxide dissolved in 50 ml water, was stirred at room temperature for 20 hours. The mixture was extracted with $CHCl_3$ and the organic layer dried ($Na_2SO_4$) and evaporated in vacuo to yield a residue. Recrystallization of the residue from ethyl acetate afforded the analytically pure products listed in Table IV.

EXAMPLE XIV

PREPARATION OF 2-ARALKYLSULFONYL-5,7-DI-n-PROPYL-1,2,4-TRIAZOLO [1,5a]PYRIMIDINE (Compounds 47–50)

A solution of 0.01 mole of 2-aralkylthio-5,7-di-n-propyl-1,2,4-triazole[1,5a]pyrimidine in 70 ml of $CHCl_3$, was cooled to 0°–5° and 4.0g (0.02 mole) of 85% m-chloroperbenzoic acid was added in portions. The mixture was allowed to stand for 24 hours at room temperature and then the $CHCl_3$ was extracted with 3 × 50 ml saturated sodium bicarbonate solution to remove unreacted m-chlorobenzoic acid. The $CHCl_3$ solution was washed with $H_2O$ (separatory funnel), dried ($Na_2SO_4$) and evaporated in vacuo to yield an oil. The oil was chilled to 0° for 2 hours, whereupon it solidified. The solid was recrystallized from n-heptane-acetone to afford the analytically pure products listed in Table IV.

EXAMPLE XV

PREPARATION OF 2-BENZYLTHIO-5-METHYL-7-(2-ACETONYL)-1,2,4-TRIAZOLO [1,5a]PYRIMIDINE (Compound 51)

A mixture of 4.12g (20 mmole) of 3-amino-5-benzylthio-1,2,4-triazole, 2.80g (20 mmole) of heptane-2,4,6-trione, 100 ml of ethanol, 100 ml benzene, and 2 drops of piperidine was refluxed in a Dean-Stark apparatus, removing about 20 ml of the water-ethanol-benzene azeotrope that formed. The solution that resulted was cooled after 6 of reflux, and the solvent was evaporated in vacuo to yield a residual, viscous orange oil. The oil was taken up in hot methanol and chilled to give a crystalline product. The product was recrystallized twice from hot methanol to afford the analytically pure product listed in Table IV. The structure was confirmed by nmr.

NMR (DMSO-$d_6$): s, 2.35 (3); s, 2.60 (3); s, 4.4 (2); s, 4.5 (2); s, 7.15 (1); m, 7.35 (5) in δ (ppm)

IR (KBr): 1730 $CM^{-1}$ (C=O)

UV (MeOH): λmax (log ε max) = 230 (3.67), 305 (3.23) mμ

Anal. ($C_{16}H_{14}N_4SO$) for C, H, N.

2-ALKYLTHIO and 2-ARALKYLTHIO-5,7-DIMETHYL-s-TRIAZOLO[1,5a]PYRIMIDINES AS 3',5'-CYCLIC AMP PHOSPHODIESTERASE INHIBITORS

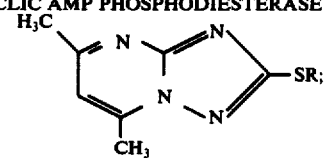

| Compound No. | R | Method of Preparation Example No. | % Yield | Mp° C | Empirical Formula | Analysis | PDE Lung;α | PDE Kidney;α |
|---|---|---|---|---|---|---|---|---|
| 3 | —H₂C—⌬ | II, III | 89 | 131–132 | $C_{14}H_{14}N_4S$ | C,H,N | 2.50 | 2.10 |
| 4 | —H₂C—⌬—CL | II | 76 | 136–137 | $C_{14}H_{13}N_4ClS$ | C,H,N | 4.00 | 4.0 |
| 7 | —CH₂—CH₂—CH3 | III | 82 | 97–98 | $C_{10}H_{14}N_4S$ | C,H,N | 0.90 | 1.00 |
| 8 | —CH(CH₃)2 | III | 60 | 95–96 | $C_{10}H_{14}N_4S$ | C,H,N | 0.10 | 1.30 |
| 9 | —CH3 | III | 76 | 154–155 | $C_8H_{10}N_4S$ | C,H,N,S | 0.50 | 0.25 |
| 10 | —CH₂—CH(CH₃)2 | III | 72 | 119–121 dec. | $C_{11}H_{16}N_4S$ | C,H, N | 0.10 | 0.50 |
| 11 | —CH(COOC₂H₅)2 | III | 85 | 109–110 | $C_{14}H_{18}N_4SO4$ | C,H,N | 0.50 | 0.00 |
| 12 | —H₂C—⌬—COOH | III | 93 | 190–193 | $C_{15}H_{14}N_4O_2S$ | C,H,N | 1.20 | 0.70 |

2-ALKYLTHIO and 2-ARALKYLTHIO-5,7-DIMETHYL-s-TRIAZOLO[1,5a]PYRIMIDINES AS 3',5'-CYCLIC AMP PHOSPHODIESTERASE INHIBITORS

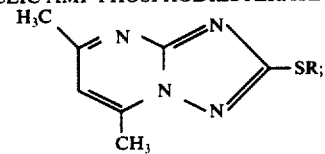

| Compound No. | R | Method of Preparation Example No. | % Yield | Mp° C | Empirical Formula | Analysis | PDE Lung;α | PDE Kidney;α |
|---|---|---|---|---|---|---|---|---|
| 13 | —H₂C—C₆H₄—CH₃ (para) | III | 95 | 124–125 | $C_{15}H_{16}N_4S$ | C,H,N | 6.20 | 1.00 |
| 14 | —H₂C—C₆H₄—CH₃ (meta) | III | 94 | 120–121 | $C_{15}H_{16}N_4S$ | C,H,N,S | 2.00 | 0.70 |
| 15 | —H₂C—C₆H₄—CH₃ (ortho) | III | 75 | 110–111 | $C_{15}H_{16}N_4S$ | C,H,N,S | 3.50 | 4.00 |
| 16 | —H₂C—(chloro-methylenedioxyphenyl) | III | 78 | 150–152 | $C_{15}H_{13}N_4SO_2Cl$ | C,H,N,S,Cl | Insoluble | |
| 17 | —H₂C—(methylnaphthyl) | III | 97 | 99–100 | $C_{19}H_{18}N_4S$ | C,H,N | Insoluble | |
| 18 | —H₂C—(4-pyridyl) | III | 75 | 143–145 | $C_{13}H_{13}N_5S$ | C,H,N,S | 0.80 | 0.70 |
| 19 | —H₂C—(3-pyridyl) | III | 75 | 164–165 | $C_{13}H_{13}N_5S$ | C,H,N | 1.17 | 0.00 |
| 20 | —H₂C—(quinolyl) | III | 87 | 175–176 | $C_{17}H_{15}N_5S$ | C,H,N,S | 2.00 | 0.70 |
| 21 | —H₂C—(furyl)—COOC₂H₅ | III | 72 | 130–131 | $C_{15}H_{16}N_4O_3S$ | C,H,N | 3.2 | 1.25 |
| 22 | —H₂C—(tetrahydrofuryl) | III | 61 | 223–224 | $C_{12}H_{16}N_4SO$ | C,H,N | 0.60 | 0.00 |

2-ALKYLTHIO and 2-ARALKYLTHIO-5,7-DIMETHYL-s-TRIAZOLO[1,5a]PYRIMIDINES AS 3',5'-CYCLIC AMP PHOSPHODIESTERASE INHIBITORS -continued

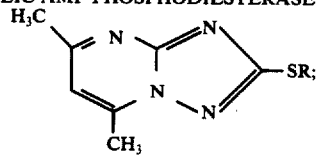

| Compound No. | R | Method of Preparation Example No. | % Yield | Mp° C | Empirical Formula | Analysis | PDE Lung;α | PDE Kidney;α |
|---|---|---|---|---|---|---|---|---|
| 23 | —H₂C—H₂C—C₆H₅ | III | 62 | 91–92 | C₁₅H₁₆N₄S | C,H,N | 2.50 | 2.50 |

TABLE II
2-BENZYLTHIO-5-METHYL-7-SUBSTITUTED-s-TRIAZOLO[1,5a]PYRIMIDINES AS 3', 5'-CYCLIC AMP PHOSPHODIESTERASE INHIBITORS

R = —CH₂—C₆H₅

| Compound No. | R1 | Method of Preparation Example No. | % Yield | Mp° C | Empirical Formula | Analysis | PDE lung;α | PDE kidney;α |
|---|---|---|---|---|---|---|---|---|
| 24 | —OH | IV | 50 | 252–253 | C₁₃H₁₂N₄OS | C,H,N,S | 0.75 | 0.75 |
| 25 | —Cl | V | 70 | 95–96 | C₁₃H₁₁N₄SCl | C,H,N | 4.00 | 1.40 |
| 26 | NH—CH₂—CH₂—CH3 | VI | 65 | 250–252 | C₁₆H₁₉N₅S | C,H,N | 2.00 | 0.90 |
| 27 | N(C₂H₅)2 | VI | 83 | 249–250 | C₁₇H₂₁N₅S | C,H,N | 4.20 | 2.30 |
| 28 | N(CH₃)2 | VI | 92 | 140–142 | C₁₅H₁₇N₅S | C,H,N,S | 8.00 | 3.40 |
| 29 | N(CH₂—CH₂OH)2 | VI | 72 | 174–175 | C₁₇H₂₁N₅O₂S | C,H,N | 2.10 | 2.30 |
| 30 | —N(piperidinyl) | VI | 62 | 89–90 | C₁₈H₂₁N₅S | C,H,N,S | 10.0 | 3.20 |
| 31 | —N(morpholinyl) | VI | 64 | 118–120 | C₁₇H₁₉N₅OS | C,H,N | 7.70 | 4.80 |
| 32 | —NH—NH₂ · 2HCl | VI | 85 | 220–223 | C₁₃H₁₆N₆SCl2 | C,H,N | Insoluble | |
| 33 | —N—N(CH₃)2 | VI | 71 | 181–183 | C₁₅H₁₇N₆S | C,H,N | 5.30 | 8.00 |
| 51 | CH₂COCH3 | XV | 47 | 133–134 | C₁₆H₁₄N₄SO | C,H,N | | |

TABLE III
2-BENZYLTHIO-6-CARBETHOXY-7-SUBSTITUTED-s-TRIAZOLO[1,5a]PYRIMIDINES AS 3',5'-CYCLIC AMP PHOSPHODIESTERASE INHIBITORS

R = —CH₂—C₆H₅

| Compound No. | R1 | Method of Preparation Example No. | % Yield | Mp° C | Empirical Formula | Analysis | PDE lung;α | PDE kidney;α |
|---|---|---|---|---|---|---|---|---|
| 34 | OH | VIII | 63 | 246–247 | C₁₅H₁₄N₄O₃S | C,H,N | 0.00 | 0.00 |
| 35 | Cl | IX | 73 | 127–129 | C₁₅H₁₃ClN₄O₂S | C,H,N | Insoluble | |
| 36 | —N(morpholinyl) | X | 70 | 92–94 | C₁₉H₂₁N₅O₃S | C,H,N | 6.90 | 2.90 |

TABLE III-continued
2-BENZYLTHIO-6-CARBETHOXY-7-SUBSTITUTED-s-TRIAZOLO[1,5a]PYRIMIDINES AS 3',5'-CYCLIC AMP PHOSPHODIESTERASE INHIBITORS Structure: EtOOC-substituted triazolo[1,5-a]pyrimidine with -SR; R = -CH$_2$-phenyl, and R$_1$ substituent

| Compound No. | R1 | Method of Preparation Example No. | % Yield | Mp° C | Empirical Formula | Analysis | PDE lung;α | PDE kidney;α |
|---|---|---|---|---|---|---|---|---|
| 37 | -NH-CH$_2$-phenyl | X | 75 | 114-116 | C$_{22}$H$_{21}$N$_5$O$_2$S | C,H,N | Insoluble | |
| 38 | NH-CH$_2$-CH$_2$OH | X | 65 | 168-170 | C$_{17}$H$_{19}$N$_5$O$_3$S | C,H,N | Insoluble | |
| 39 | NH-CH$_2$-CH$_2$-CH3 | X | 85 | 94-6 | C$_{18}$H$_{21}$N$_5$O$_2$S | C,H,N | 21.0 | 7.0 |
| 40 | -SH | XI | 80 | 133-136 | C$_{15}$H$_{14}$N$_4$O$_2$S2 | C,H,N | Insoluble | |

TABLE IV
2-ARALKAYLTHIO and HETEROARALKAYLTHIO-5,7-DI-n-PROPYL and 5-n-PROPYL-7-ACETONYL s-TRIAZOLE[1,5-a]PYRIMIDINES Structure: CH$_3$CH$_2$CH$_2$-substituted triazolo[1,5-a]pyrimidine with -XR, and R$_1$ substituent

| Compound No. | R1 | X R | Method of Preparation Example No. | % Yield | Mp°C | Empirical Formula | Analysis |
|---|---|---|---|---|---|---|---|
| 41 | CH$_2$CH$_2$CH3 | SCH$_2$-phenyl | XI | 77 | 59-61 | C$_{18}$H$_{22}$N$_4$S | C, H, N |
| 42 | CH$_2$CH$_2$CH3 | SH | XII | 57 | 142-148 | C$_{11}$H$_{16}$N$_4$S | C, H, N |
| 43 | CH$_2$CH$_2$CH3 | SCH$_2$-phenyl-CH$_3$ | XIII | 77 | 67-68 | C$_{19}$H$_{24}$N$_4$S | C, H, N |
| 44 | CH$_2$CH$_2$CH3 | SCH$_2$-phenyl-CO$_2$H | XIII | 24 | 147-149 | C$_{19}$H$_{22}$N$_4$SO2 | C, H, N |
| 45 | CH$_2$CH$_2$CH3 | SCH$_2$-pyridyl(N) | XIII | 27 | 151-152 | C$_{17}$H$_{21}$N$_5$S.H$_2$SO4 | C, H, N |
| 46 | CH$_2$CH$_2$CH3 | SCH$_2$-pyridyl(N) | XIII | 27 | 128-129 | C$_{17}$H$_{21}$N$_5$S.H$_2$SO4 | C, H, N |
| 47 | CH$_2$CH$_2$CH3 | SO$_2$-CH$_2$-phenyl | XIV | 47 | 109-111 | C$_{18}$H$_{22}$N$_4$O$_2$S | C, H, N |
| 48 | CH$_2$CH$_2$CH3 | SO$_2$-CH$_2$-phenyl-CH$_3$ | XIV | 80 | 106-107 | C$_{19}$H$_{24}$N$_4$O$_2$S | C, H, N |
| 49 | CH$_2$CH$_2$CH3 | SO$_2$-CH$_2$-phenyl-CO$_2$H | XIV | 57 | 169-170 | C$_{19}$H$_{22}$N$_4$SO4 | C, H, N |
| 50 | CH$_2$CH$_2$CH3 | SO$_2$-CH$_2$-pyridyl(N) | XIV | 22 | 162-163 | C$_{17}$H$_{21}$N$_5$O$_2$S.H$_2$SO4 | C, H, N |

EXAMPLE XVI

The compounds of this invention have been tested for their ability to inhibit action of the enzyme phosphodiesterase, and the results are shown in the tables which follow.

3',5'-Cyclic AMP phosphodiesterase (PDE) has been isolated and purified from two different tissues in the following manner. Homogenates of rabbit lung and kidney were made in sucrose-Tris-magnesium buffer and were subjected to centrifugation at low speed to remove nuclei and cell debris. The supernatants were then centrifuged at 105,000x g for 30 minutes. The 105,000x g supernatants were then fractionated using (NH$_4$)$_2$SO$_4$. The precipitation which formed at 0-30% saturation was collected by centrifugation at 20,000x g and dissolved in Tris-magnesium buffer and dialyzed overnight against the same buffer. A second (NH$_4$)$_2$SO$_4$ fraction was obtained by raising the concentration of the first supernatant to 50%. These two (NH$_4$)$_2$SO$_4$ fractions as well as the supernatant from the 30–50% cut were then assayed for PDE activity using the method of Appleman, *Biochemistry* 10, 311 (1971). The first fraction obtained from lung and kidney tissues was found to contain a PDE with low affinity for 3′,5′-cyclic AMP (high Km). The second fraction was found to exhibit a biphasic curve when the Lineweaver-Burk method of analysis was used. This indicates either the presence of two separate enzymes, one having a high and the other a low affinity for the enzymes, or one protein with two separate sites. Appleman, supra, indicates that extracts of brain yield two separate enzymes (a high Km and a low Km) which can be separated by sepharose gel chromatography.

All of the inhibitory studies reported here were performed with the high affinity (Fraction II, low Km) enzyme obtained from rabbit lung and kidney. I$_{50}$ values were calculated in some instances from a plot of log I vs. percent I in experiments in which inhibitor concentration was varied over a wide range, at a constant 3,5′-cyclic AMP concentration of approximately 1.7 × 10$^{-7}$M. The relative inhibitory activity of each compound as compared with theophylline is expressed as an $\alpha$ value. This value is obtained by dividing the I$_{50}$ Valve for the theophylline in a particular experiment by the I$_{50}$ value obtained for the particular compound being evaluated. In most instances $\alpha$ values were calculated from an inhibition study performed with a single concentration of test compound as long as the inhibition produced by that concentration was from 20–80%. In this instance an $\alpha$ value was calculated by dividing the concentration of theophylline giving the same (X%) inhibition
concentration of test substance giving X% inhibition.

The validity of this method has been checked by comparing $\alpha$ values obtained by (1) measurements at a single concentration of inhibitor and (2) measurements at four concentrations of inhibitor (I$_{50}$ determinations). $\alpha$ Values compared in this way have been found to agree to within 10% of each other.

The basic incubation mixture contained the following substances (amounts in $\mu$moles): $^3$H-cAMP (specific activity ~2, 180 cmp/pmole), 0.00016; Tris pH 7.5, 40; MgCl$_2$, 0.5; Enzyme (cAMPphosphodiesterase), 5–50 $\mu$g protein; and 10$^{-4}$ to 10$^{-6}$ molar concentration of the inhibitor; incubation time 10 minutes at 30° C. At the end of incubation the mixtures are heated to 90° C for 2 minutes and 100 $\mu$g of snake venom phosphodiesterase from Crotalus atrox was added and the tubes incubated for 10 minutes at 30° C. The mixture was then cooled and 1 ml of a Dowex 1-2X, 200–400 mesh suspension, prepared by mixing 100 g of the resin in 200 g H$_2$O, was added and the mixture centrifuged. An aliquot of the supernatant was used to determine counts per minute using a liquid scintillation spectrometer. Zero time values were obtained using incubations in which the cAMP phosphodiesterase was omitted from the first incubation.

Analysis of the results set forth in the foregoing tables indicates that several of the compounds of this invention possess inhibition capability significantly superior to theophylline and in some cases, as for example, Compounds 28, 30 and 33, on the order of 8 to 10 times greater. Moreover, these results clearly indicate that such compounds possess selective phosphodiesterase enzyme inhibitory capability. With respect to the compounds which are indicated in Tables I, II and III as being insoluble, although such compounds have not undergone the inhibitory test of Example XVI, due to the similarity in structure to compounds which were tested, it is expected that in vivo testing of the compounds in forms other than solution will readily indicate phosphodiesterase enzyme inhibitory capability. It should likewise be indicated that the various R substituents set forth in the examples of Table I could be utilized in place of the benzyl substituent of Tables II and III and that the resulting compounds would inhibit phosphodiesterase enzymes.

Preliminary pharmacological evaluation has revealed that 2-benzylthio-7-hydroxy-5-methyl-s-triazolo[1,5$a$]-pyrimidine (Compound 24), 2-benzylthio-7-[bis($\beta$-hydroxyethyl)amino]-5-methyl-s-triazolo[1,5$a$]pyrimidine (Compound 29), 2-benzylthio-7-diethylamino-5-methyl-s-triazole[1,5$a$]pyrimidine (Compound 27 ) and 2-benzylthio-6-carbethoxy-7-n-propylamino-s-triazolo[1,5$a$]pyrimidine (Compound 39) all possess the ability to bring about coronary dialation at a concentration of 10 $\mu$g/ml in an isolated guinea pig heart preparation. Additionally, it has been observed that 2-benzylthio-7-[bis($\beta$-hydroxyethyl)amino]-5-methyl-s-triazolo[1,5$a$]pyrimidine (Compound 29) has also been found to produce a positive inotropic effect at a concentration of 10 $\mu$g/ml in the isolated guinea pig heart preparation.

Additionally pharmacological evaluation has revealed that 2-benzylthio-7-hydroxy-5-methyl-s-triazolo[1,5$a$]pyrimidine (Compound 24), 2-benzylthio-7-[bis($\beta$-hydroxyethyl) amino]-5-methyl-s-triazolo[1,-5$a$]pyrimidine (Compound 29), and 2-benzylthio-7-diethylamino-5-methyl-s-triazolo [1,5$a$]pyrimidine (Compound 27) are smooth muscle relaxants as evidenced by their ability to relax isolated guinea pig uteri at concentrations of 2–10 $\mu$g/ml.

Following the procedure of C. A. Winter, et al as described in the Proc. Exper. Biol. Med., 111, 544 (1962) for the evaluation of a compound's anti-inflammatory properties, has revealed that 2-benzylthio-7-hydroxy-5-methyl-s-triazolo[1,5$a$]pyrimidine (Compound 24) has significant activity when administered orally to rats at a dose of 100 mg/kg of body weight. At this dose, there was a 43% inhibition of foot volume.

Compound 32 (2-benzylthio-7-hydrazino-5-methyl-s-triazolo[1,5$a$]pyrimidine) has been found to possess significant hypotensive activity as determined by the method of J. R. Weeks and J. A. Jones, J. Pharm. Exper. Therap., 104, 646 (1960). At an oral dose of 50 mg/kg in rats, there was a % decrease in mean blood pressure at 1, 3, 6 hours of 11%, 13%, and 24%, respectively. This same compound had significant hypotensive activity at an oral dose of 25 mg/kg in the rat.

EXAMPLE XVII

Compounds 3, 41, 43–48, 51 were tested in anesthetized dogs for hemodynamic activities including cardiac output, stroke volume and heart rate. For management of low perfusion states such as cardiovascular shock and congestive heart failure, it is desirable to have increased cardiac output and increased stroke volume accompanied by a decrease or no change in heart rate. At a dose of 10 mg/Kg/hr, Compounds 41, 43–48 (2-benzylthio-5,7-di-n-propyl-1,2,4-triazolo[1,5$a$]pyrimidine; 5,7-di-n- propyl-2-(4-methylbenzyl)thio-1,2,4-triazolo[1,5a]-pyrimidine; 5,7-di-n-propyl-2-(4-carboxybenzyl)thio-1,2,4-triazolo[1,5a]pyrimidine; 5,7-di-n-propyl-2-(4-picolyl)thio-1,2,4-triazolo[1,5a]pyrimidine; 5,7-di-n-propyl-2-(3-picolyl)thio-1,2,4-triazolo[1,5a]pyrimidine; 2-benzylsulfonyl-5,7-di-n-propyl-1,2,4-triazolo[1,5a]-pyrimidine; and 5,7-di-n-propyl-2-(4-methylbenzyl)sulfonyl-1,2,4-triazolo[1,5a]pyrimidine) respectively, showed significant increases in cardiac output and stroke volume while showing a decrease or nominal change in heart rate.

TABLE V

CARDIOVASCULAR ACTIVITY OF 2-ARALKYLTHIO AND HETEROARALKYLTHIO-5,7-DI-ALKYL-s-TRIAZOLO[1,5a]PYRIMIDINES

% CHANGE OF CARDIAC OUTPUT, STROKE VOLUME AND HEART RATE AT 10 mg/Kg/hr

TABLE V

CARDIOVASCULAR ACTIVITY OF 2-ARALKYLTHIO-AND HETEROARALKYLTHIO-5,7-DI-ALKYL-s-TRIAZOLO[1,5a]PYRIMIDINES

% CHANGE OF CARDIAC OUTPUT, STORAGE VOLUME AND HEART RATE AT 10 mg/Kg/hr

| Compound Number | Vehicle | Cardiac Output | Stroke Volume | Heart Rate |
|---|---|---|---|---|
| 3 | DMSO | −1 | −7 | −7 |
| 41 | DMSO | +23 | +27 | −4.2 |
| 43 | DMSO | +34.3 | +3.8 | −2.8 |
| 44 | Saline | +18 | +18 | +0.2 |
| 45 | Saline | +27 | +39 | −8.1 |
| 46 | Saline | +20 | +35 | −10.9 |
| 47 | DMSO | +35.6 | +34.7 | +0.2 |
| 48 | DMSO | +16.4 | +36.1 | −14.3 |
| 51 | DMSO | +46.2 | +42.0 | +3.3 |

We claim:
1. A compound of the structure

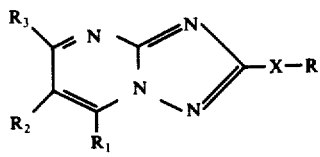

wherein X is thio or sulfonyl; R is $C_2$–$C_6$ alkyl, $C_3$–$C_7$ branched alkyl, dicarbethoxymethyl, benzyl, substituted benzyl wherein the substitutions are $C_1$–$C_6$ alkyl, halogeno, carboxy, hydroxyl or a combination of those substituents, naphthyl and phenethyl; $R_1$ is $C_1$–$C_6$ alkyl; $R_2$ is H and $R_3$ is $C_1$–$C_6$ alkyl or acetonyl.

2. The compound of claim 1 wherein X is thio or sulfonyl; R is benzyl or substituted benzyl wherein the substitutions are $C_1$–$C_6$ alkyl, halogeno, carboxy, hydroxyl or a combination of these substituents, or R is phenethyl; $R_1$ is $C_1$–$C_3$ alkyl; $R_2$ is H; and $R_3$ is $C_1$–$C_3$ alkyl.

3. The compound of claim 1 wherein X is thio; R is benzyl; $R_1$ is n-propyl; $R_2$ is H; and $R_3$ is n-propyl.

4. The compound of claim 1 wherein X is sulfonyl; R is benzyl, $R_1$ is n-propyl; $R_2$ is H; and $R_3$ is n-propyl.

5. The compound of claim 1 wherein X is thio, R is 4methyl-benzyl; $R_1$ is n-propyl; $R_2$ is H; and $R_3$ is n-propyl.

6. The compound of claim 1 wherein X is thio, R is benzyl; $R_1$ is acetonyl; $R_2$ is H; and $R_3$ is n-propyl.

7. The compound of claim 1 wherein X is sulfonyl; R is 4-methylbenzyl; $R_1$ is n-propyl; $R_2$ is H; and $R_3$ is n-propyl.

8. A compound of the structure

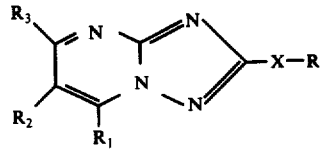

wherein X is thio or sulfonyl; R is benzyl or substituted benzyl wherein the substitutions are halogeno, carboxy, hydroxyl or a combination of those substituents, $C_1$–$C_6$ alkyl; $R_1$ is an amine selected from the group consisting of $NHR^1$, $N(R^1)_2$, $N-N(R^1)_2$ where $R^1$ is a $C_1$–$C_6$ alkyl or substituted alkyl where the substitution is hydroxyl or $R_1$ is piperidino, morpholino or the dihydrochloride salt of hydrazine; $R_2$ is H; and $R_3$ is $C_1$–$C_6$ alkyl.

9. Benzylthio-7-[bis($\beta$-hydroxyethyl)amino]-5-methyl-s-triazolo-[1,5-$a$]pyrimidine.

10. Benzylthio-7-diethylamino-5-methyl-s-triazolo[1,5-$a$]pyrimidine.

11. Benzylthio-7-hydrazino-5-methyl-s-triazolo[1,5-$a$]pyrimidine.

12. 2-(4-Carboxybenzyl)thio-5,7-di-n-propyl-s-triazolo[1,5-$a$]-pyrimidine.

* * * * *